United States Patent
Squire et al.

[11] Patent Number: 6,091,980
[45] Date of Patent: Jul. 18, 2000

[54] STENT SLIP SENSING SYSTEM AND METHOD

[75] Inventors: James C. Squire, Everett; Campbell Rogers, Westwood; Elazer R. Edelman, Brookline, all of Mass.

[73] Assignee: Massachusetts Institute of Technology, Cambridge, Mass.

[21] Appl. No.: 09/225,282

[22] Filed: Jan. 5, 1999

Related U.S. Application Data

[60] Provisional application No. 60/085,097, May 12, 1998.

[51] Int. Cl.$^7$ .................................................. A61F 11/00
[52] U.S. Cl. ........................... 600/381; 600/373; 606/108
[58] Field of Search ..................................... 600/373, 381; 606/108, 192, 194, 195, 198; 128/899

[56] References Cited

U.S. PATENT DOCUMENTS

| | | |
|---|---|---|
| 4,665,918 | 5/1987 | Garza et al. . |
| 4,944,740 | 7/1990 | Buchbinder et al. . |
| 5,108,416 | 4/1992 | Ryan et al. . |
| 5,158,548 | 10/1992 | Lau et al. . |
| 5,242,399 | 9/1993 | Lau et al. . |
| 5,266,073 | 11/1993 | Wall . |
| 5,409,019 | 4/1995 | Wilk . |
| 5,433,216 | 7/1995 | Sugrue et al. . |
| 5,470,350 | 11/1995 | Buchholtz et al. . |
| 5,607,442 | 3/1997 | Fischell et al. . |
| 5,651,047 | 7/1997 | Moorman et al. . |
| 5,665,103 | 9/1997 | Lafontaine et al. . |
| 5,697,377 | 12/1997 | Wittkampf ............................... 128/899 |
| 5,879,297 | 3/1999 | Haynor et al. ........................... 600/407 |
| 5,902,238 | 5/1999 | Golden et al. ........................... 600/424 |
| 5,913,820 | 6/1999 | Bladen et al. ........................... 600/407 |
| 5,921,924 | 7/1999 | Avitall ..................................... 600/374 |
| 5,928,248 | 7/1999 | Acker ...................................... 606/108 |
| 5,944,023 | 8/1999 | Johnson et al. ......................... 128/899 |
| 5,983,126 | 11/1999 | Wittkampf ............................... 600/509 |

*Primary Examiner*—Paul J. Hirsch
*Assistant Examiner*—Michael B. Priddy
*Attorney, Agent, or Firm*—Samuels, Gauthier & Stevens, LLP

[57] ABSTRACT

An endoluminal device slippage sensor system including an electrically conductive endoluminal device and a catheter assembly to which the device is coupled for deployment into a lumen. First, second and third electrodes are associated with the catheter assembly, each respectively in direct electrical contact with a proximal, a middle and a distal portion of the device. A potential source generates a potential between the first and second electrodes and between the second and third electrodes. The potential between the electrodes is varied in accordance with a change of position of the device along the axis of the catheter assembly during deployment in which the proximal or distal portion of the device is disconnected from the first or third electrode, respectively. In accordance with another embodiment of the invention there is provided an endoluminal device slippage sensor system including an electrically conductive endoluminal device and a catheter assembly to which the device is coupled for deployment into a lumen. At least two electrodes are mounted longitudinally along the length of the catheter assembly, each of the electrodes being in direct electrical contact with the device. A potential source generates a potential between the electrodes, the potential between the electrodes being varied in accordance with a change of position of the device along the axis of the catheter assembly.

15 Claims, 3 Drawing Sheets

STENT SLIP SENSING SYSTEM AND METHOD

PRIORITY INFORMATION

This application claims priority from provisional application Ser. No. 60/085,097 filed May 12, 1998.

BACKGROUND OF THE INVENTION

The invention relates to the field of catheter delivered stents, and in particular to a catheter slip sensor.

Slippage or loosening of a stent on the delivery catheter impairs the accuracy of stent placement in up to 10% of all procedures, yet current stent delivery technologies do not inform the operator of slip until after the stent is irreversibly expanded. This is especially important given the rapidly increasing popularity of many stent designs (there were over 200,000 endovascular stents implanted in the U.S. in 1996) and the fact that clinical failure of a stent implantation may occur with placement errors as small as a few millimeters.

An endovascular stent is a hollow, expandable tubular structure that is mounted over a catheter and is threaded through a hemostatic valve into the vasculature. Once positioned, it is expanded by either inflating a luminally-mounted balloon or by retracting a restraining sheath that permits the elastic stent to spring open.

Slippage can occur as the stent passes into the artery through the hemostatic valve, or more commonly, while navigating tortuous vasculature. This second cause of slip occurs in a two-stage process: leading edge separation and edge snare. As the catheter is pushed through a sharp curvature, it bends more abruptly than the stent. This causes a separation between the catheter and the distal end of the stent along the outer edge of the curvature. The leading edge of the stent now protrudes beyond the catheter profile, and becomes ensnared in the arterial bend.

Stent slip on the delivery catheter is difficult to directly measure. The majority of endovascular stent designs, including the two currently approved by the FDA, are only slightly radio-opaque, making stent placement difficult. The majority of stenting systems crimp the stent over radio-opaque markers on the delivery catheter to provide the operator with indirect evidence of the stent location under fluoroscopy. This indirect method is inaccurate and misleading if the stent slips. The operator, unaware of the displacement, may attempt to deploy the stent once the catheter markings are positioned within the stenosed region, resulting in inaccurate placement, incomplete expansion, or total nondeployment of the stent. The success of the stent positioning can be ascertained only after deployment, through indirect angiographic evidence of the flow patterns of radio-opaque dye though the stented vessel.

There are more serious ramifications of the operator being unaware of a displaced stent than inaccurate placement. If the stent begins to loosen on its delivery catheter it can slide off entirely once its protective sheath is retracted. If the stent dislodges in the distal direction it may enter into the circulation, requiring emergency surgery for retrieval. If it slides too far proximally it will not deploy and then can later slip over the balloon in the distal direction as the balloon is being retracted into the guide catheter. These issues could be avoided if the operator could sense displacement of the stent along the delivery catheter, as the operator could then opt to either retrieve and recrimp the stent before retracting the guide catheter or deploy the stent immediately before greater risk of stent displacement is encountered.

The danger of stent movement on the guide catheter is evinced by the variety of means that have been proposed to negate it. As discussed below, none have proved entirely effective. There is a device that detects the presence or absence of the distal region of a stent against the catheter, but it cannot measure the position of the stent along the catheter nor detect proximal slippage. The system we propose is capable of detecting both a proximal and distal dislodgment of the stent as well as measure the relative position of the stent against the catheter. In one embodiment it can further provide information about localized regions of detachment, such as occur just prior to axial slip when advancing the catheter past a tight arterial bend. We have constructed a prototype, as detailed below, and have demonstrated its feasibility.

SUMMARY OF THE INVENTION

It is an object of the invention to improve upon the design of the catheter assembly used to deploy endoluminal stents. Specifically, the invention demonstrates how miniature resistive electrical sensors attached to the catheter may be employed to provide the operator with real-time information concerning the relative position of the stent relative to the catheter. This information can warn the operator of clinically important conditions such as unwanted slippage of the entire stent along the axis of the catheter during catheter placement, or separation of a region of the stent from the catheter during navigation of small-radius arterial bends.

In accordance with one embodiment of the invention there is provided an endoluminal device slippage sensor system including an electrically conductive endoluminal device and a catheter assembly to which the device is coupled for deployment into a lumen. First, second and third electrodes are associated with the catheter assembly, each respectively in direct electrical contact with a proximal, a middle and a distal portion of the device. A potential source generates a potential between the first and second electrodes and between the second and third electrodes. The potential between the electrodes is varied in accordance with a change of position of the device along the axis of the catheter assembly during deployment in which the proximal or distal portion of the device is disconnected from the first or third electrode, respectively.

In accordance with another embodiment of the invention there is provided an endoluminal device slippage sensor system including an electrically conductive endoluminal device and a catheter assembly to which the device is coupled for deployment into a lumen. At least two electrodes are mounted longitudinally along the length of the catheter assembly, each of the electrodes being in direct electrical contact with the device. A potential source generates a potential between the electrodes, the potential between the electrodes being varied in accordance with a change of position of the device along the axis of the catheter assembly.

DETAILED DESCRIPTION OF THE INVENTION

Figure 1:
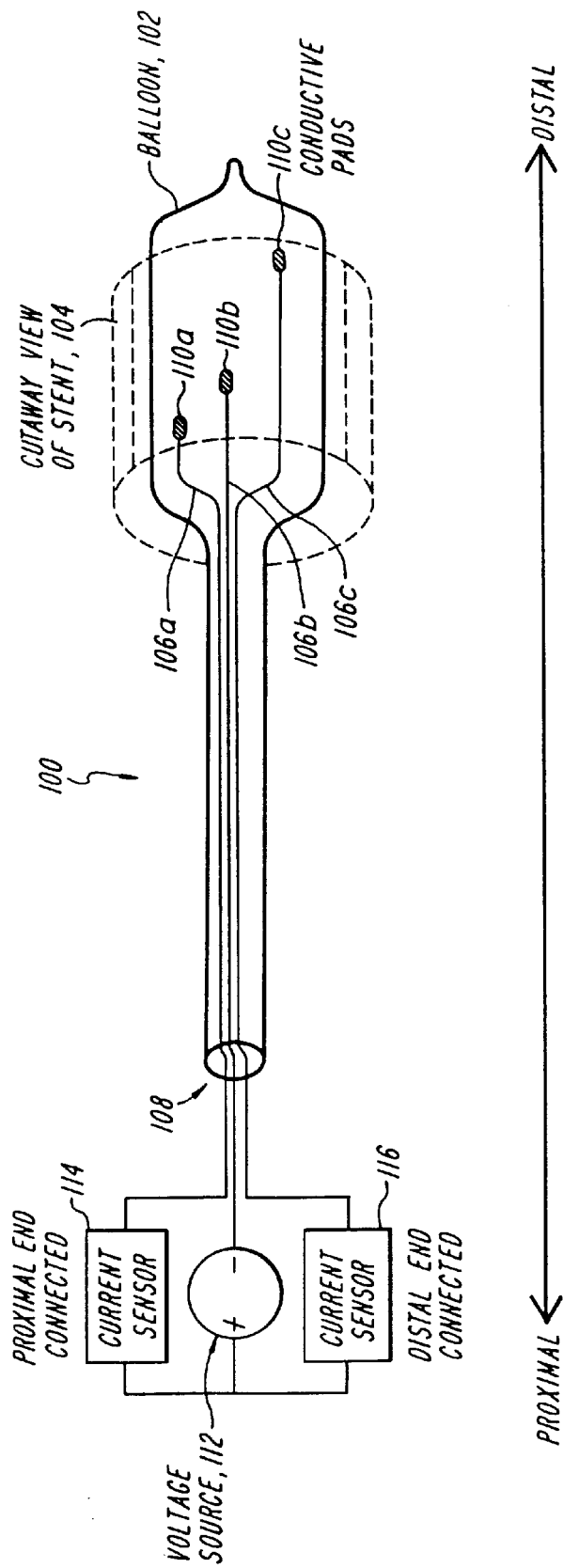
FIG. 1 is a functional block diagram of a stent slippage sensing system in accordance with the invention.

FIG. 1 is a functional block diagram of a stent slip sensing system 100 in accordance with the invention. The system includes a delivery balloon catheter 102 and a stent 104 that is positioned at the distal end of the catheter. The stent is shown in a cutaway view. Three conductors 106a, 106b, 106c run from a proximal port 108 of the catheter (held by the operator) to the outer surface of the balloon. The conductors are surrounded by insulation except at their terminus on the balloon, where they are bared to form conductive pads 110a, 110b, 110c. The conductive pads are positioned at each of the proximal, one-third or mid-proximal, and distal ends of the balloon, respectively.

The electrically conductive stent is mounted over the conductors, sandwiching them in place next to the balloon. A small voltage difference is applied from a voltage source 112 between the middle conductor 106b and each of the end conductors 106a, 106c. The current that flows from the center conductive pad 110b, through the stent 104, and out the end conductors 110a, 110c is monitored via current sensors 114, 116. If the stent begins to slip in the distal direction away from the operator, current will cease through the proximally mounted conductive pad 110a. Similarly, a proximal slip of the stent will stop current through the distal conductive pad 110c. The voltage source is current-limited to <10 µA at a frequency of 1 kHz to comply with FDA regulations.

Figure 2:
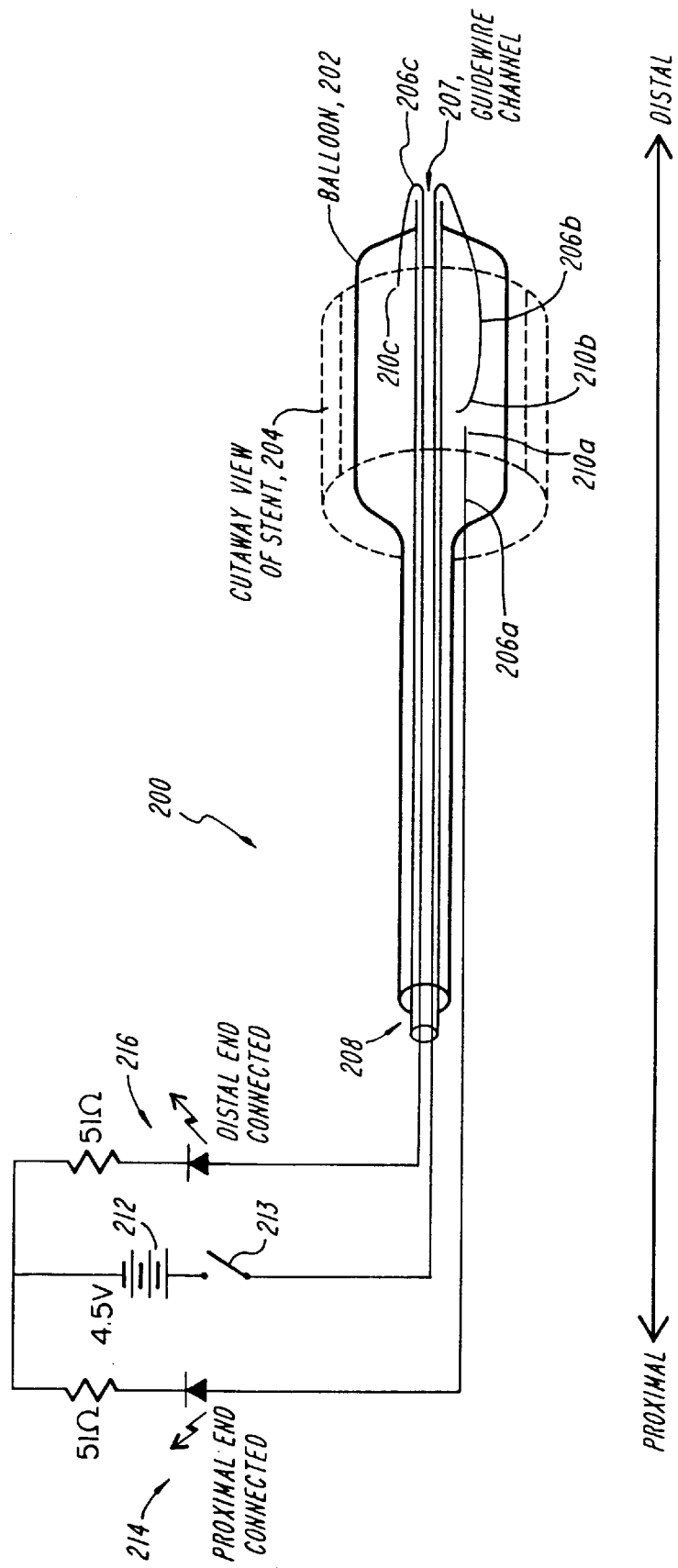
FIG. 2 is a functional block diagram of an alternative embodiment of a stent slippage sensing system.

FIG. 2 is a functional block diagram of a stent slip sensing system 200 in accordance with an alternative embodiment of the invention. The system 200 includes a balloon catheter 202 and a stent 204. The catheter, for example, can be a 3 mm compliant angioplasty type as manufactured by Advanced Cardiovascular Systems (ACS). The stent, for example, can be a 3 mm MultiLink stent as manufactured by ACS.

Three 40 gauge enameled copper wires run from a proximal port 208 of the catheter (held by the operator) to the outer surface of the balloon. Each of the wires has a 1 mm bared end for use as a conductive region 210a, 210b, 210c. The conductive regions could alternatively be configured from a conductive polymer embedded into the catheter or a metallic foil lining the catheter stem.

Two of the wires 206b, 206c are threaded through a mechanical guide wire channel 207 of the catheter. The third wire 206a is wrapped on the outside of the catheter. The proximal wire ends are secured in place by wrapping them around the catheter base, and the distal ends are secured and electrically connected by crimping them onto the balloon. Different sensitivities of slip can be obtained by varying the offset between the distal/middle and proximal/middle pairs of contacts.

A small voltage difference is applied from a voltage source 212 via a switch 213 between the middle conductor 206b and each of the end conductors 206a, 206c. The current that flows from the center conductive pad 210b, through the stent 204, and out the end conductors 210a, 210c is monitored via current sensors 214, 216. Electrical resistance varies from approximately 25 Ω when connected, to more than 10 kΩ when slip occurs in a ionic (PBS) bath that simulates a blood/vascular tissue environment. To comply with FDA regulations, in clinical use the contact sensor would be driven by an alternating current voltage source, typically 10 kHz, that would be current limited to 10 µA. In a prototype system, a 6-volt battery DC source is used to generate the difference in sensor resistance so as to drive a light-emitting diode through a current limiting 51 Ω resistor.

Figure 3:
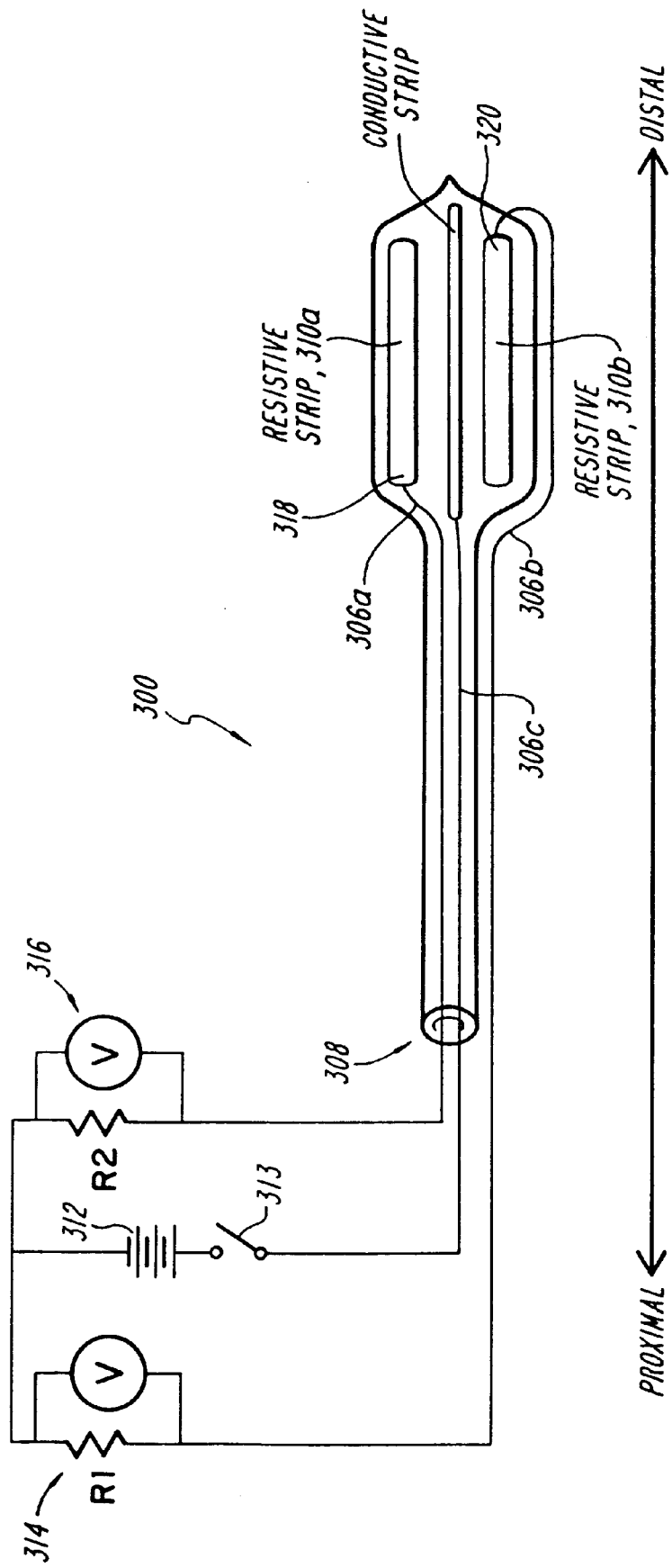
FIG. 3 is a functional block diagram of another alternative embodiment of a stent slippage sensing system.

In another alternative embodiment of the invention, a continuous measurement of the location of the stent relative to the catheter is obtained. FIG. 3 is a functional block diagram of a stent slip sensing system 300. The system 300 includes a balloon catheter 302 and an electrically conductive stent (not shown). A pair of resistive strips 310a, 310b are mounted axially along the length of the balloon catheter, and a third conductive strip 311 is mounted on the catheter parallel to, but not touching the resistive strips. The strips also include conductive wires 306a, 306b, 306c, respectively, coupled to a proximal port 308. The resistive strips 310a, 310b can be fabricated from a material such a Nichrome, and the conductive strip 311 from a material such as aluminum. Each strip can be , for example, 50 µm thick, 0.5 mm wide, and 3 mm long. When the stent is positioned on the catheter, it is in electrical contact with each of the strips.

A voltage/current source 312 (e.g. 100 µA) supplies a current to the center conductive strip 311 via a switch 313, which then flows through the electrically-conductive stent and into both resistive strips. The current next proceeds out the proximal end 318 of one resistive strip and the distal end 320 of the other resistive strip, through fixed resistors R1 and R2 of two voltage sensors 314, 316, and back into the voltage/current source. Resistors R1 and R2 each form voltage dividers with the resistive strips, and the voltage developed across them is monitored. The resistance of the fixed resistors R1 and R2 should be of the same magnitude as the resistance of the resistive strips, which for the Nichrome example illustrated is approximately 500 Ω.

When the stent is properly positioned it shorts both resistive strips to the conductive strip, and the entire voltage from the voltage source is developed across R1 and R2. As the stent slips proximally, current must flow through a portion of the distally attached resistive strip 310b, and the resultant decrease in voltage drop across R1 measures the new proximal stent position. As the stent slips distally, a similar decrease in the voltage developed across R2 tracks the distal position. A further improvement would add more resistive strips with alternating proximal and distal attachment points evenly spaced around the balloon catheter surface. This would permit detection and measurement of localized regions of stent/catheter detachment, such as occurs when passing the catheter around tight arterial bends just prior to stent slip.

Although the present invention has been shown and described with respect to several preferred embodiments thereof, various changes, omissions and additions to the form and detail thereof, may be made therein, without departing from the spirit and scope of the invention. For example, while the invention is illustrated using a cardiac endovascular stent as the most commonly used variety of stent, it will be appreciated that the system of the invention could be successfully used to deploy and measure slippage of any expandable endoluminal device.

What is claimed is:

1. An endoluminal device slippage sensor system comprising:
   an electrically conductive endoluminal device;
   a catheter assembly to which said device is coupled for deployment into a lumen;
   first, second and third electrodes associated with said catheter assembly, each respectively in direct electrical contact with a proximal, a middle and a distal portion of said device; and
   a potential source which generates a potential between said first and second electrodes and between said second and third electrodes, said potential between said electrodes being varied in accordance with a change of position of said device along the axis of said catheter assembly during deployment in which said proximal or distal portion of said device is disconnected from said first or third electrode, respectively.

2. The system of claim 1, wherein said endoluminal device comprises an endovascular stent.

3. The system of claim 1, wherein said catheter assembly comprises a balloon catheter.

4. The system of claim 1 further comprising at least one potential sensor which monitors the potential variations between said electrodes.

5. The system of claim 1, wherein said potential source comprises a voltage source.

6. An endoluminal device slippage sensor system comprising:

an electrically conductive endoluminal device;

a catheter assembly to which said device is coupled for deployment into a lumen;

at least two electrodes mounted longitudinally along the length of said catheter assembly, each of said electrodes being in direct electrical contact with said device; and a potential source which generates a potential between said electrodes, said potential between said electrodes being varied in accordance with a change of position of said device along the axis of said catheter assembly.

7. The system of claim 6, wherein said endoluminal device comprises an endovascular stent.

8. The system of claim 1, wherein said catheter assembly comprises a balloon catheter.

9. The system of claim 1 further comprising at least one potential sensor which monitors the potential variations between said electrodes.

10. The system of claim 1, wherein said potential source comprises a voltage source.

11. The system of claim 1 further comprising at least a third electrode mounted longitudinally along the length of said catheter assembly and being in direct electrical contact with said device.

12. The system of claim 11, wherein said at least two electrodes comprise resistive electrodes.

13. The system of claim 12, wherein said at least a third electrode comprises a conductive electrode.

14. A method of sensing slippage of an electrically conductive endoluminal device which is coupled to a catheter assembly for deployment into a lumen, comprising:

providing at least two electrodes longitudinally along the length of said catheter assembly, each of said electrodes being in direct electrical contact with said device; and generating a potential between said electrodes, said potential between said electrodes being varied in accordance with a change of position of said device along the axis of said catheter assembly.

15. A method of sensing slippage of an electrically conductive endoluminal device which is coupled to a catheter assembly for deployment into a lumen, comprising:

providing at least two electrodes longitudinally along the length of said catheter assembly, each of said electrodes being in direct electrical contact with said device; and generating a potential between said electrodes, said potential between said electrodes being varied in accordance with a change of position of said device along the axis of said catheter assembly.

* * * * *